United States Patent
Papandreas

[19]

[11] Patent Number: 5,931,667
[45] Date of Patent: Aug. 3, 1999

[54] ORTHODONTIC APPARATUS AND METHOD

[76] Inventor: Samuel G. Papandreas, 14193 Basswood Cir., Strongsville, Ohio 44136

[21] Appl. No.: 08/892,035

[22] Filed: Jul. 14, 1997

[51] Int. Cl.$^6$ ...................................................... A61C 3/00
[52] U.S. Cl. ................................. 433/8; 433/9; 433/10; 433/17; 433/24
[58] Field of Search .................................. 433/8, 10, 17, 433/18, 24, 9

[56] References Cited

U.S. PATENT DOCUMENTS

| | | |
|---|---|---|
| D. 359,776 | 6/1995 | Hilgers . |
| 3,738,005 | 6/1973 | Cohen et al. . |
| 3,936,939 | 2/1976 | Faunce . |
| 4,107,844 | 8/1978 | Kurz ............................................ 433/9 |
| 4,470,809 | 9/1984 | Klepacki ................................. 433/9 X |
| 4,533,320 | 8/1985 | Piekarsky ............................... 433/10 X |
| 4,573,913 | 3/1986 | Creekmore . |
| 4,609,350 | 9/1986 | Krause . |
| 4,766,704 | 8/1988 | Brandestini et al. . |
| 5,027,281 | 6/1991 | Rekow et al. . |
| 5,169,311 | 12/1992 | Lee ......................................... 433/24 X |
| 5,184,306 | 2/1993 | Erdman et al. . |
| 5,184,955 | 2/1993 | Baer et al. ............................. 433/24 X |
| 5,356,288 | 10/1994 | Cohen . |
| 5,374,187 | 12/1994 | Vashi . |
| 5,452,219 | 9/1995 | Dehoff et al. . |
| 5,464,349 | 11/1995 | Andreiko et al. .......................... 433/24 |
| 5,474,448 | 12/1995 | Andreiko et al. . |
| 5,518,397 | 5/1996 | Andreiko et al. . |

*Primary Examiner*—Nicholas D. Lucchesi
*Attorney, Agent, or Firm*—Jones, Day, Reavis & Pogue

[57] ABSTRACT

Orthodontic brackets having tubular passages are bonded to at least six teeth in an upper or lower human dental arch, including at least two teeth other than molars, and a super-flexible archwire is extended through all of the passages. The orthodontic brackets are non-metallic thin veneer bodies having tubular passages for receiving the archwire. Custom veneer bodies are fabricated using information obtained from a model or a sectioned model of a patient's dental arch, or from digital mapping of the patient's tooth surfaces or the facsimile tooth surfaces in the model. The orientation of each tubular passage in each bracket depends upon the desired final position of each tooth, and upon the degree of torque, tip and angulation required for achieving such position. Contrary to the prior practice of making orthodontic brackets as small as possible, the veneer bodies have a large bonding surface area that covers much of a tooth facial surface and corresponds with the facial surface shape of the tooth.

42 Claims, 9 Drawing Sheets

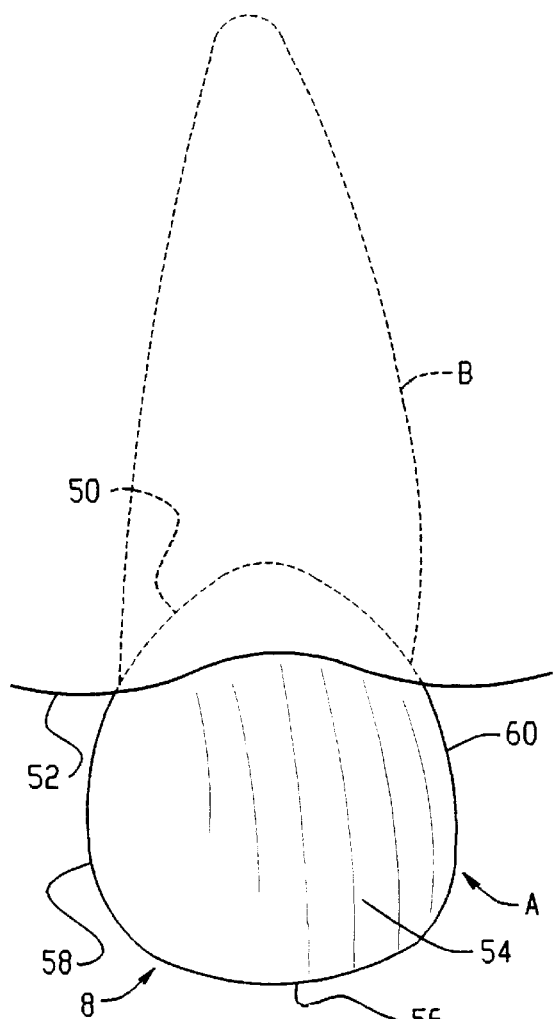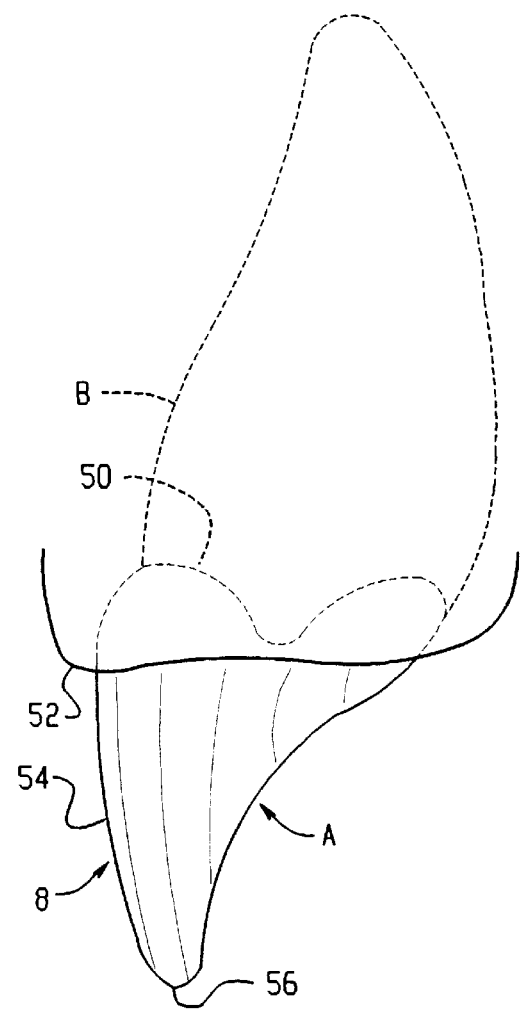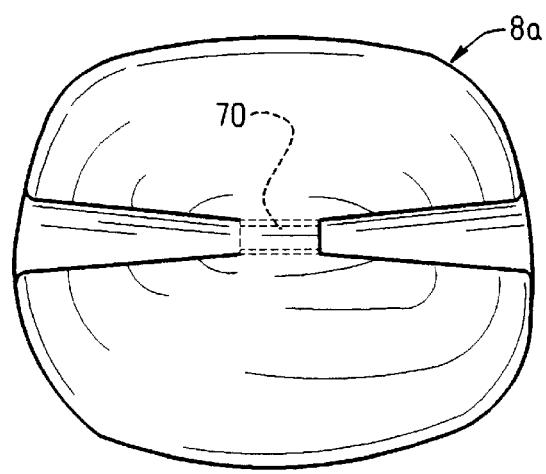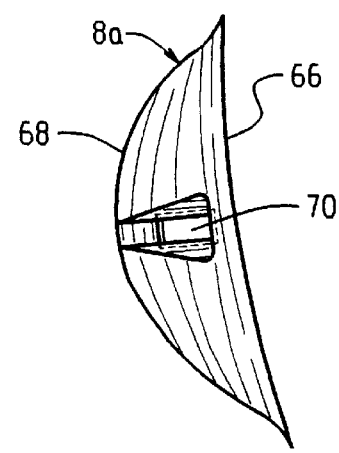

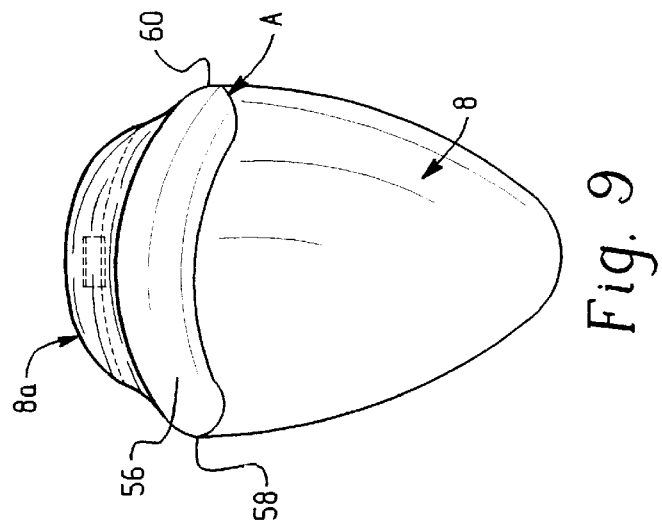
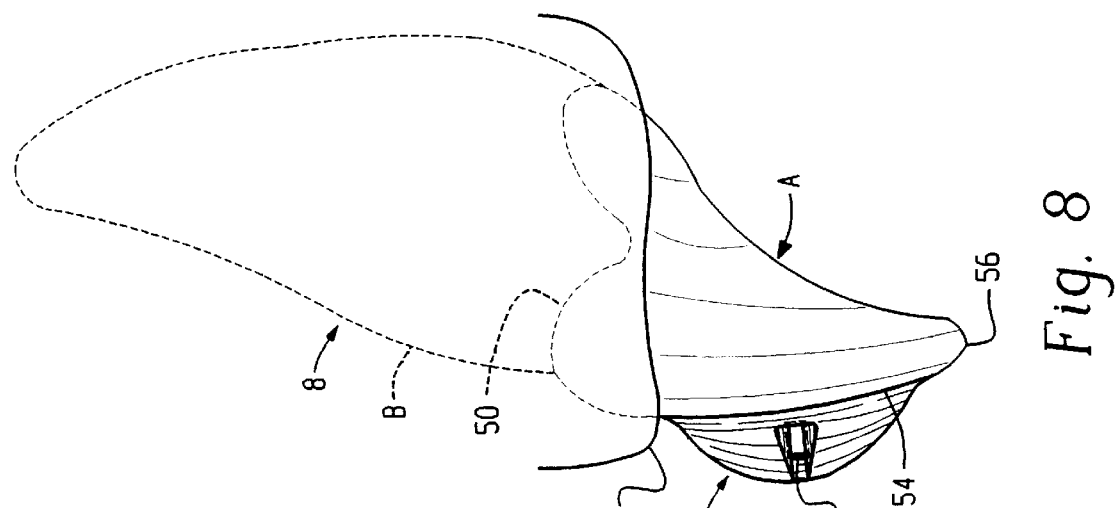
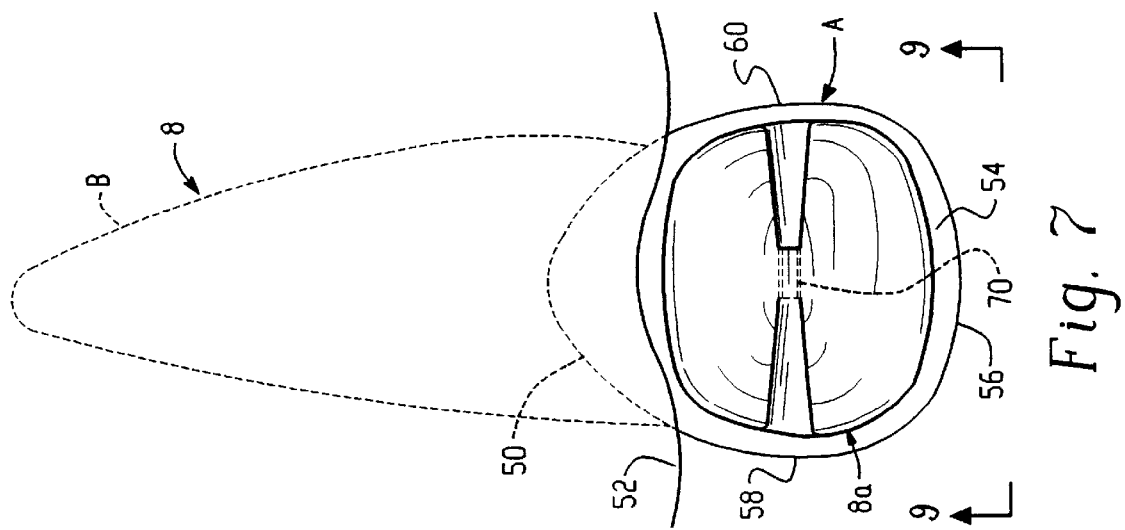

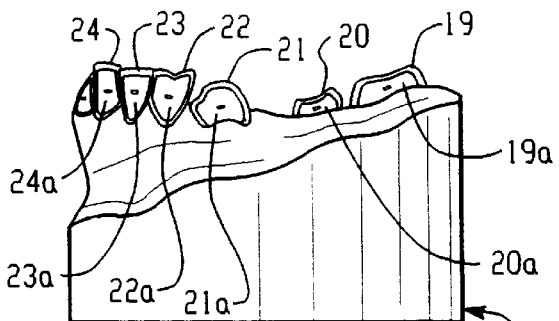
Fig. 24
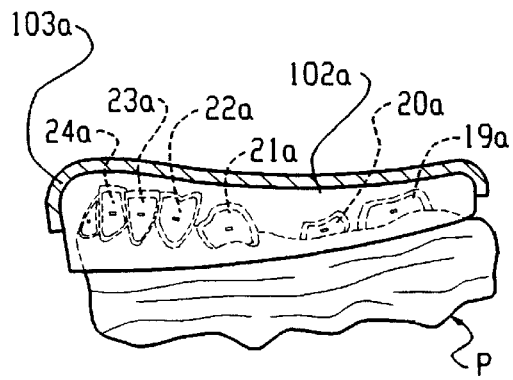
Fig. 27
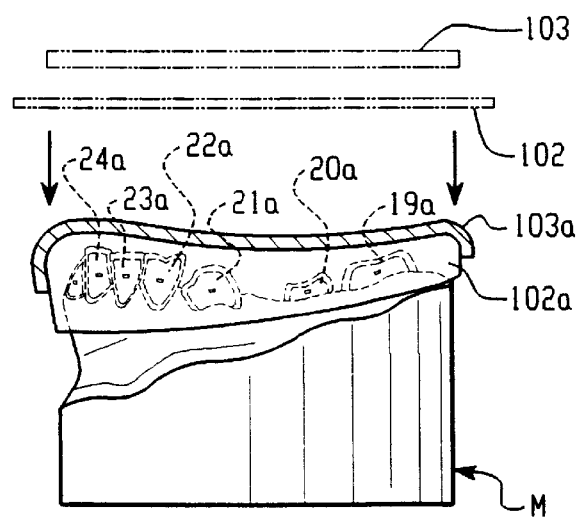
Fig. 25
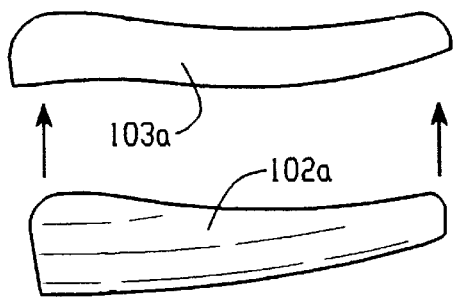
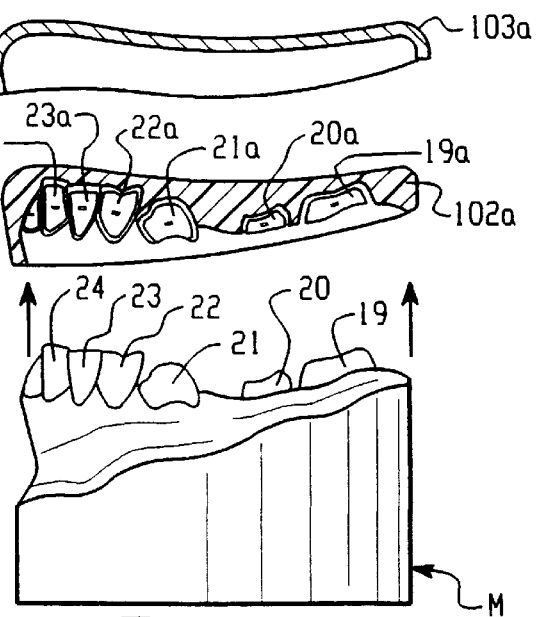
Fig. 26
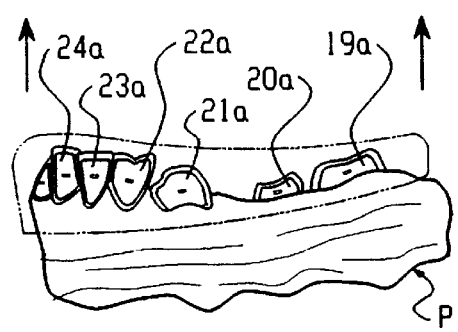
Fig. 28

ORTHODONTIC APPARATUS AND METHOD

BACKGROUND OF THE INVENTION

This application relates to the art of orthodontics and, more particularly, to an improved orthodontic apparatus and method. The invention is particularly applicable to the use of an improved thin veneer body orthodontic bracket and will be described with specific reference thereto. However, it will be appreciated that the invention has broader aspects and that certain features of the invention can be carried out with conventional orthodontic brackets.

It is routine to correct misalignment of teeth in a dental arch by bonding brackets to tooth facial surfaces and attaching an archwire to the brackets. The archwire exerts forces of very low magnitude on the teeth through the brackets for moving misaligned teeth to desired positions over extended periods of time. The brackets that are applied to the molars commonly have tubes in which end portions of the archwire are received. The brackets that are bonded to teeth other than molars have outwardly open slots receiving an archwire which is retained in the slots by elastic bands or by locking devices on the brackets.

In arrangements of the type described, the brackets usually are made as small as possible in an attempt to minimize their unsightly appearance. This provides a very small bonding area between a bracket and tooth, and the brackets are susceptible to detachment by failure of the bond. This problem cannot be overcome solely by the use of stronger adhesives because the adhesive must be one that permits eventual removal of the brackets without destroying tooth enamel.

Brackets that project relatively far outwardly from a tooth facial surface are prone to being dislodged by forces generated while biting and chewing food. The same problem exists with brackets that have irregular, angular or sharp geometric forms due to the presence of projections, grooves and archwire locking devices. These brackets also are subject to buildup of impacted food, plaque and calculus which cause stains, cavities and periodontal disease. Unlike the normal tooth contour that protects gum tissue by deflecting food away from the gums, brackets that have a relatively high profile and angular surfaces often deflect food into the gums in a manner that causes damage to gum tissue. Archwires that are held in place by bands or locking devices require frequent office visits to reposition the archwires relative to the orthodontic brackets as the teeth move.

Historically, archwires used with orthodontic brackets were quite rigid. The archwire was permanently deformed at selective locations for applying desired forces to certain teeth, and frequent adjustments were necessary. Even after the development of highly flexible archwires, orthodontic brackets with outwardly open slots continued to be used on all teeth except the first and second molars. Because the use of slots, bands and locking devices is taught in dental schools and has been employed with success for many years, there is a very strong mind-set in favor of continuing to use them and against making any significant changes. What is familiar usually is preferred over what is unknown. It is a misconception that bands or locking devices are necessary on individual brackets for adjustment purposes in order to obtain desired corrections.

It would be desirable to overcome the aforementioned problems, as well as others, by providing a new procedure for correcting misaligned teeth and to provide an improved orthodontic bracket for use in carrying out the procedure.

SUMMARY OF THE INVENTION

Orthodontic brackets bonded to facial surfaces of teeth in a human dental arch include at least six brackets having tubular passages through which a superflexible archwire extends. The brackets with tubular passages are used on the four molars in a dental arch and preferably on at least two bicuspids.

Brackets with tubular passages preferably are used on as many teeth as possible, and the number is limited only by the severity of the malocclusion for individual teeth. Where a malocclusion for an individual tooth is too severe to thread a superflexible archwire through a tubular passage in a bracket bonded to the tooth, one or more conventional brackets with slots may be used.

Although conventional brackets with tubular passages may be used to correct misaligned teeth in accordance with the present application, a preferred arrangement uses an improved very low profile orthodontic bracket that comprises a thin non-metallic veneer body having a tubular passage therein for receiving an archwire.

In a preferred arrangement, the veneer body is molded of ceramic, plastic or a combination of the two materials. The desired shape and size of the veneer body may be provided by machining or molding, or by a combination thereof.

The tubular passage may be provided by molding it into the veneer body, by molding a metal tube into the veneer body, by machining a slot into the veneer body and bonding a tube of metal or other suitable material in the slot, or by broaching a rectangular tubular passage in the veneer body. When the tubular passage is broached or molded, a tube of metal or other suitable material may or may not be adhesively bonded into the passage. In accordance with another aspect of the invention, the veneer body is dimensioned to cover most of a tooth facial surface, and is tinted to match the appearance of the patient's teeth. The large area of the veneer body provides a more secure bond between the veneer body and a tooth facial surface to minimize the possibility of dislodgment. The large area of the veneer body also provides a more natural appearance for a patient's exposed dental arch.

In one arrangement, improved orthodontic brackets are fabricated by first making a model of a patient's dental arch. The optimum position and inclination of each tube in each bracket for each tooth is then determined by use of the model. For example, the model may be sectioned into individual teeth which are then moved to desired final positions for use in fabricating the veneer bodies.

In another arrangement, tooth shape data may be digitized from the patient's teeth or from the model. The data is then used to determine the desired final tooth position and to fabricate appropriate veneer bodies with the tubular passages oriented for cooperation with an archwire to achieve the appropriate correction. The facial surface shapes of the patient's teeth or the model teeth are used to machine or mold the rear bonding surfaces of the brackets so that each bonding surface generally corresponds to the shape of the tooth facial surface to which the bracket is bonded.

The improved brackets with integral tubes most preferably are applied to all of the teeth in a patient's dental arch. However, it will be recognized that it is possible to use other brackets on certain individual teeth, such as brackets having outwardly open slots, in cases of extreme tooth misalignment. The teeth on which other brackets are used will usually be one or more of the incisors, although slotted brackets also may be used on one or more bicuspids for severe malocclusions.

Brackets with tubular passages are used on at least six teeth in one dental arch, and more preferably are used on all but 1–3 of the teeth in a dental arch. When the brackets with tubular passages are used on just six teeth in a dental arch, at least two of the teeth are not molars. The principal reason for the possible use of slotted brackets on 1–3 teeth is that the misalignment is so bad that the archwire could not be threaded through a tube. Once the tooth has been moved sufficiently by use of a slotted bracket, a bracket with a tubular passage may be substituted for the slotted bracket.

After the brackets are bonded to a patient's teeth, a highly flexible archwire is threaded through the tubular passages in all of the brackets. The superflexible archwire is not stressed beyond its elastic limit at any location throughout its length and exerts force on the teeth through the brackets as it tries to assume its original unstressed configuration.

The archwire preferably is an alloy such as nickel-titanium or copper-nickel-titanium, although other alloys and materials can be used. The archwire is preformed to an unstressed generally U-shaped original configuration to substantially match the size and curvature of a patient's upper or lower dental arch when the patient's teeth are in their desired final positions.

Universal brackets may be fabricated for use on many patients without custom fabricating brackets for each individual patient. This also permits the use of universal brackets on many of a patient's teeth while custom fabricating only those brackets that are necessary for certain individual teeth.

It is a principal object of the invention to provide an improved arrangement for correcting is aligned teeth by using orthodontic brackets having tubular passages for receiving an archwire on at least six teeth in a human dental arch.

It is another object of the present invention to provide an improved low profile orthodontic bracket.

It is also an object of the invention to provide an orthodontic bracket in the form of a nonmetallic thin veneer body having a tubular passage for receiving an archwire.

It is a further object of the invention to provide an improved method for correcting misalignment of teeth.

BRIEF DESCRIPTION OF THE DRAWING

FIG. 3 is a front plan view of an individual tooth;

FIG. 4 is a side elevational view of the tooth of FIG. 3;

FIG. 5 is a front elevational view of an orthodontic bracket;

FIG. 6 is a side elevational view of the orthodontic bracket of FIG. 5;

FIG. 7 is a front elevational view of a tooth having an orthodontic bracket attached thereto;

FIG. 8 is side elevational view of a tooth having an orthodontic bracket attached thereto;

FIG. 9 is an end view of the tooth of FIGS. 7 and 8 having the orthodontic bracket attached thereto;

FIG. 24 is a side elevational view of a model of a patient's lower dental arch having brackets releasably attached to the facial surfaces of the teeth in the model;

FIG. 25 is a side elevational view similar to FIG. 21 and showing two separate sheets of thermoplastic material molded over the model teeth and brackets to provide a flexible transport tray and a relatively rigid stabilizing tray;

FIG. 26 is a side elevational view showing the model of the lower dental arch with the brackets trapped in the flexible plastic transfer tray and with the rigid stabilizing tray releasably positioned over the upper portion of the flexible transport tray;

FIG. 27 shows the plastic transfer and stabilizing trays with the orthodontic brackets applied to a patient's lower dental arch; and FIG. 28 is a side elevational view showing the orthodontic brackets bonded to facial surfaces of the teeth in a patient's lower dental arch, and with the plastic stabilizing and transfer trays being removed.

DESCRIPTION OF A PREFERRED EMBODIMENT

Figure 1:
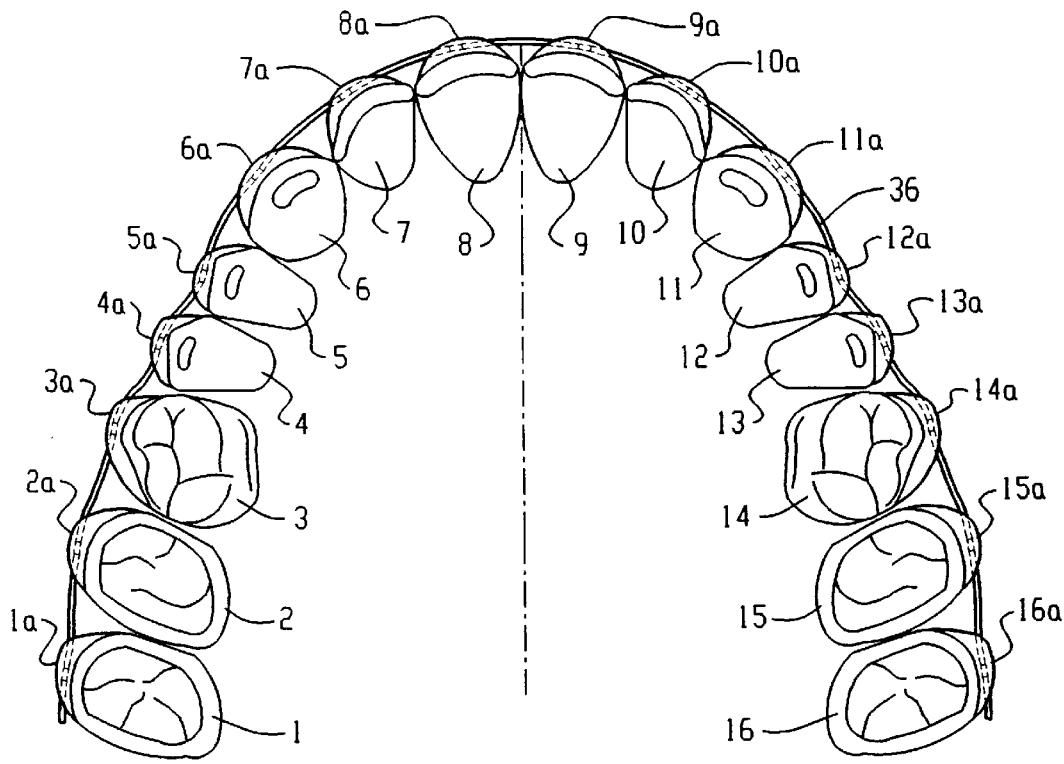
FIG. 1 is a plan view of an upper human dental arch.
Figure 2:
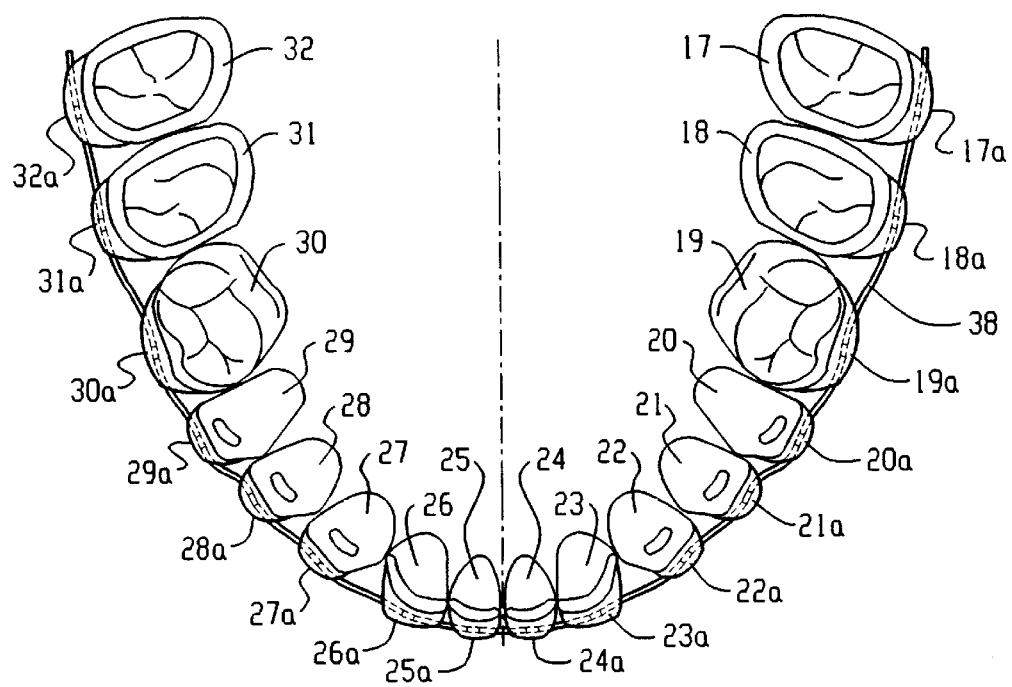
FIG. 2 is a plan view of a lower human dental arch.

Referring now to the drawing, wherein the showings are for purposes of illustrating certain preferred embodiments of the invention only and not for purposes of limiting same, FIGS. 1 and 2 show upper and lower human dental arches. The teeth are numbered consecutively starting with number 1 in the upper right of a patient's mouth and ending with number 32 in the lower right of the patient's mouth. The third molars or wisdom teeth are identified by numbers 1, 16, 17 and 32, and often are removed from a patient's mouth. The second molars are identified by numbers 2, 15, 18 and 31. The first molars are identified by numbers 3, 14, 19 and 30. The bicuspids are identified by numbers 4, 5, 12, 13, 20, 21, 28 and 29. The canines or cuspids are identified by numbers 6, 11, 22 and 27. The incisors are identified by numbers 7, 8, 9, 10, 23, 24, 25 and 26.

Low profile orthodontic brackets in accordance with the present application are shown attached to facial surfaces of teeth 1–32 and are identified by numerals 1a–32a. Superflexible archwires 36 and 38 are shown extending through tubular passages in all of the orthodontic brackets.

FIGS. 3 and 4 show a typical incisor 8 having a crown A and a root B that merge together at a cemento-enamel junction represented by line 50. Root B is anchored in bone which is covered by gum tissue that extends over the upper portion of crown A to provide a gum line generally indicated at 52. The anatomic crown of the tooth extends all the way to cemento-enamel junction 50 whereas the clinical crown extends to gum line 52. In older patients and persons with disease, at least part of the anatomic crown that normally is covered by gum tissue may be exposed.

Clinical crown A includes a facial surface 54 that faces outwardly of a patient's mouth, and has an outer periphery that includes a terminal end portion 56 and an opposite gum end portion that coincides with gum line 52, and opposite side portions 58, 60. Side portions 58 and 60 extend between terminal end portion 56 and gum line 52. It will be recognized that the size and peripheral shape of a tooth facial surface varies considerably from tooth-to-tooth and from patient-to-patient.

FIGS. 5 and 6 show an orthodontic bracket thin veneer body 8a that preferably is molded of ceramic, plastic or a combination of the two. Many different materials can be used and those that will be identified are simply by way of example rather than by way of limitation. Ceramics include $ZrO_2$, silicone dioxide, powdered quartz, alumina and mixtures of these. Plastics include methyl methacrylate, polycarbonate, polyacrylic, polyethylene, polyester and mixtures of these. The veneer body also can be a mixture of plastic and ceramic.

The improved arrangement of the present application for using orthodontic brackets having tubular passages on at least six teeth in one dental arch also can be carried out with conventional brackets of metal such as stainless steel or precious metal alloys.

Orthodontic bracket thin veneer body 8a has a peripheral shape that is similar to the peripheral shape of tooth facial surface 54. The area of veneer body 8a preferably is at least 50% of the area of tooth facial surface 54, more preferably 70% of the area of tooth facial 54 and most preferably at least 80% or more of the area of tooth facial surface 54. Ideally, a veneer body would have an area and peripheral shape that is nearly the same size and shape as a tooth facial surface to which the veneer body is applied, especially for the most visible incisors and canines.

Veneer body 8a has a rear attachment or bonding surface 66 that substantially conforms to the surface contour of tooth facial surface 54 and is bonded thereto with dental sealant or other dental adhesive. Veneer body 8a has an outer surface 68 that supplants tooth facial surface 54 when veneer body 8a is bonded thereto. The large area of rear bonding surface 66 on veneer body 8a provides a very secure bond to the tooth facial surface and minimizes the possibility of veneer body dislodgment. The extended area of the veneer body also minimizes staining and decay of visible facial surfaces of the teeth.

The veneer bodies are tinted to match the color and shading of the tooth facial surfaces in a patient's mouth. The low profile contoured outer surfaces of the veneer bodies allows them to blend in and provide a more natural appearance. In the embodiment illustrated in FIGS. 5–16, a rectangular tubular passage 70 is molded integrally into veneer body 8a for receiving an archwire. The longitudinal axis of passage 70 extends transversely in a direction between opposite sides 58 and 60 of tooth facial surface 54.

Tubular passage 70 can be rotated in the plane of the paper to vary its inclination and can also be tipped in or out of the plane of the paper to control the direction of the forces applied to a tooth by the archwire. Tubular passage 70 also can be moved to other positions rather than the approximate center of the veneer body, and can be rotated about its own axis to different rotated positions prior to being formed in or attached to the veneer body. These selective positions of the tubular passage relative to a bracket cooperate with the archwire to provide corrections that commonly are referred to as torque, tip and angulation.

FIGS. 7–9 show orthodontic bracket veneer body 8a bonded to a facial surface 54 of tooth clinical crown A. The veneer body is shown covering most of the exposed facial surface of the tooth, and this is particularly desirable for the highly visible incisors and canines.

Figure 10:
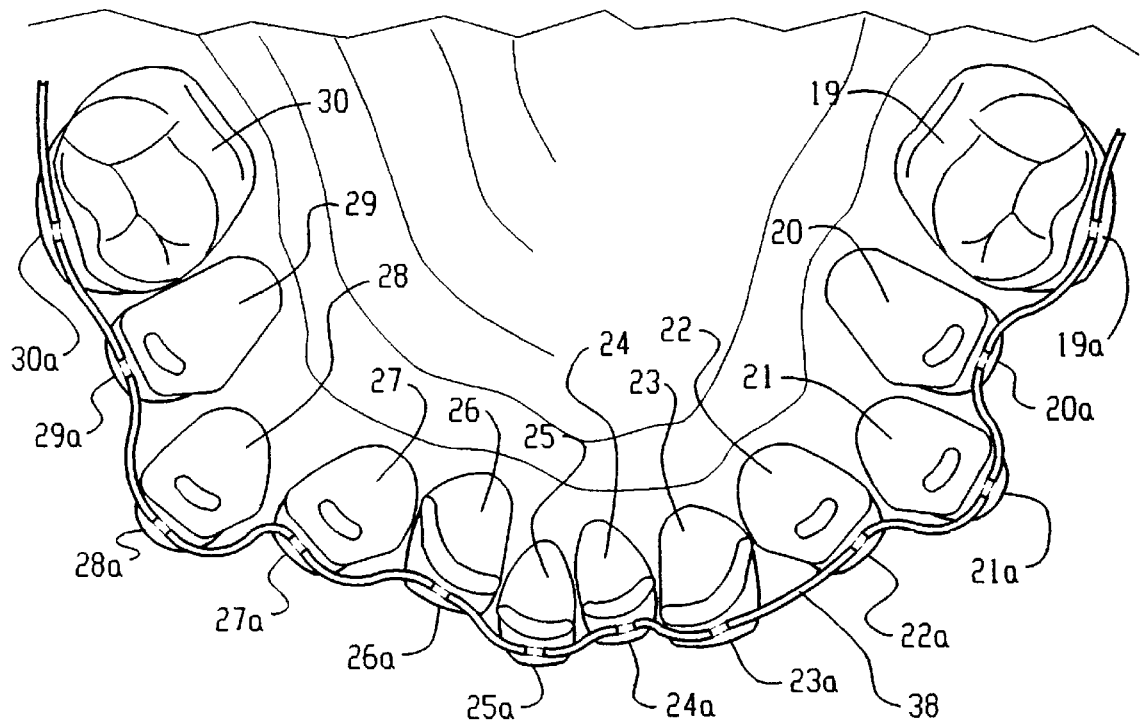
FIG. 10 is a partial plan view of a lower human dental arch with misaligned teeth.

FIG. 10 shows a portion of a lower dental arch with misaligned teeth. Orthodontic bracket veneer bodies are bonded to the tooth facial surfaces and superflexible archwire 38 is threaded through all of the tubular passages in all of the dental brackets. Forces applied to the teeth by archwire 38 through the dental brackets over a long period of time move the teeth to the positions shown in FIG. 2. As previously mentioned, wisdom teeth 1, 16, 17 and 32 often have been removed from a patient's dental arch but can be included in a correction procedure when they are still present and will not be extracted.

Threading of the superflexible archwire through the tubular passages can start with any desired bracket. For example, any of brackets 1a, 16a, 17a or 32a could be a starting point for progressively threading one end of an archwire through all of the tubular passages. Any intermediate bracket can also be selected as a starting point. For example, one end of the archwire may be threaded through bracket 7a in a direction toward bracket 6a, and that end of the archwire is then threaded through the tubular passages in all of brackets 7a–1a. The opposite end of the archwire is threaded through bracket 8a in the opposite direction toward bracket 9a and progressively is threaded through all of brackets 8a–16a.

The archwire is preformed to have an unstressed generally U-shaped configuration that substantially matches the size and curvature of the patient's dental arch when the teeth are in their desired final positions. The archwire is placed in bending stress when it is threaded through all of the tubular passages but is not bent beyond its elastic limit anywhere along its entire length. The inherent nature of the archwire material to relieve the bending stress and return to its smooth U-shaped configuration applies forces to the misaligned teeth through the brackets.

Figure 11:
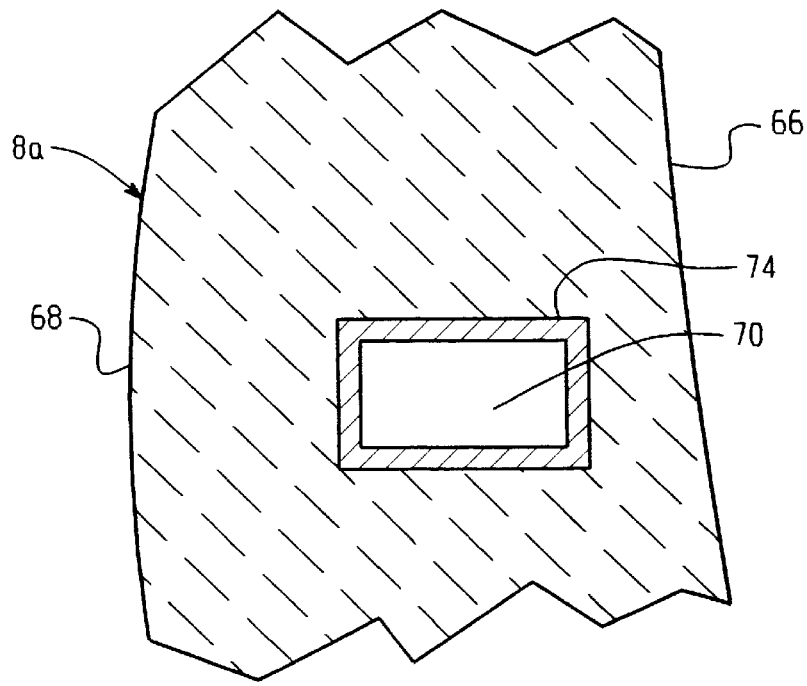
FIG. 11 is an enlarged partial cross-sectional elevational view showing a tube molded into an orthodontic bracket.
Figure 12:
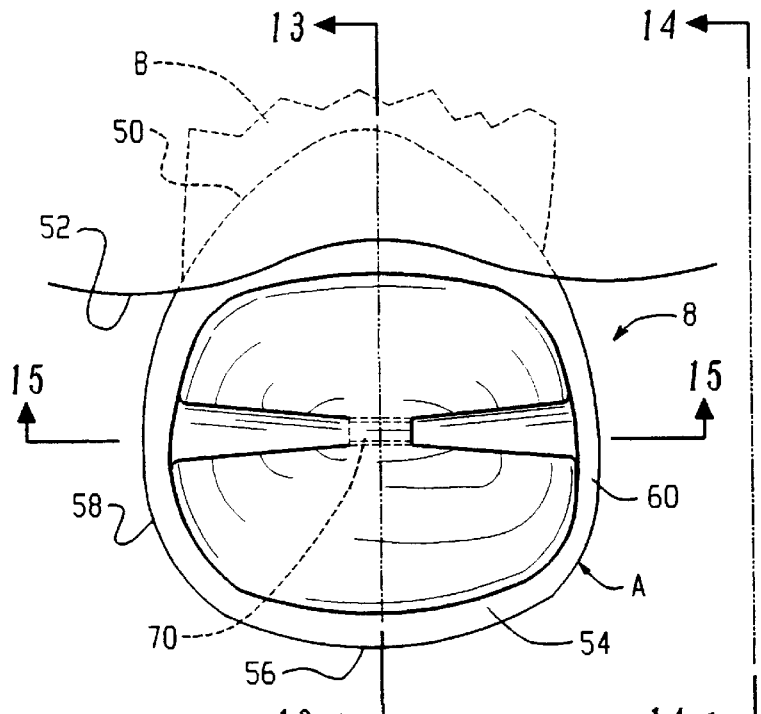
FIG. 12 is a front elevational view of a crown portion of a tooth having an orthodontic bracket attached thereto.
Figure 13:
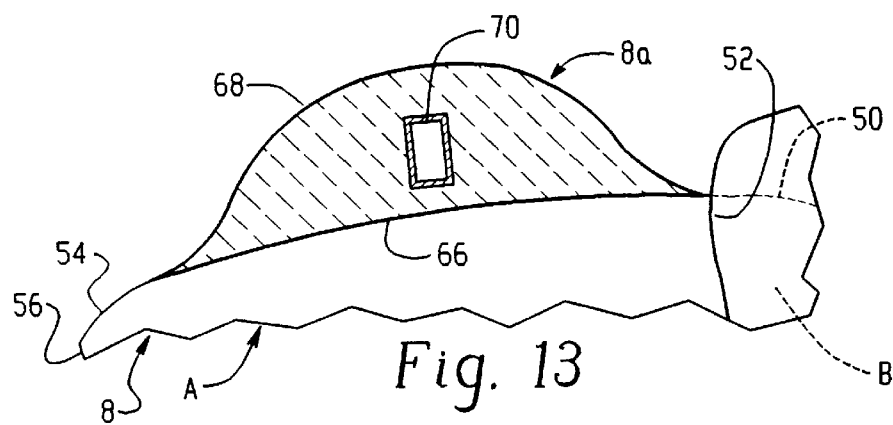
FIG. 13 is a cross-sectional elevational view taken generally on line 13—13 of FIG. 12.

FIG. 11 shows peripherally continuous rectangular tubular passage 70 as being defined by the rectangular inner peripheral surface of a rectangular metal tube 74 that may be of stainless steel or precious metal alloy, or of other suitable materials such as ceramic, plastic or a combination of the two. Although the metal tube is shown in the preferred form as being rectangular, it will be recognized that for certain purposes other shapes such as cylindrical are also possible for ease of fabrication.

Tube 74 is positioned with its cross-sectional long dimension extending generally perpendicular to rear bonding surface 66 and with its cross-sectional short dimension extending generally parallel to rear attachment surface 66. It will be recognized that tube 74 can be rotated about its own longitudinal axis in FIG. 11 to vary its position within veneer body 8a and thereby vary the direction of forces applied to a tooth by the archwire. In the arrangement shown, tube 74 is positioned substantially closer to rear bonding surface 66 than to veneer body facial surface 68 but could be closer to veneer body facial surface 68.

The cross-sectional size of the opening provided by tube 70 is not critical but usually has sides that are between about 0.04–0.07 mm. For example, the cross-sectional length or long dimension may be about 0.06 mm while the cross-sectional width or short dimension may be about 0.04 mm. The wall thickness of tube 74 may be around 0.03 mm. Obviously, the opening and wall thickness may have many different dimensions and those mentioned are simply by way of example. The distance from rear attachment surface 66 to the centerline of tubular passage 70 preferably is not greater than about 2 mm. Veneer body 8*a*, along with all other orthodontic bracket veneer bodies, has a maximum thickness that is not greater than about 4 mm and more preferably not greater than about 2 mm.

The length of peripherally closed tubular passage 70 preferably is between 1–5 mm and most preferably is not less than about 2 mm. The opposite open ends of tubular passage 70 are spaced inwardly from the opposite peripheral sides of the veneer body. Although the tube is shown substantially centered with respect to a veneer body, it will be recognized that it can be positioned closer to the top or bottom of a veneer body as well as closer to one of the veneer body sides. The tube also can be tipped in the plane of the paper or perpendicular to the plane of the paper. In the latter case, the distance from the centerline of the tubular passage to the rear bonding surface will vary along the length of the centerline.

Figure 15:
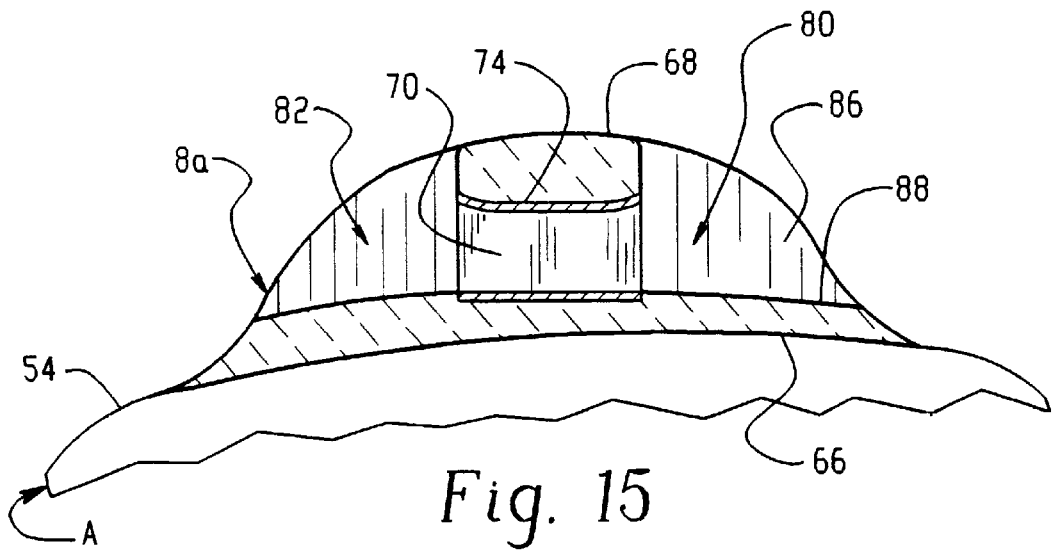
FIG. 15 is a cross-sectional elevational view taken generally on line 15—15 of FIG. 12.

The end portions of the tubular passage may be flared outwardly to facilitate threading of the archwire into the passage. Outward flaring of the upper end portions of a tubular passage is illustrated in FIG. 15. It will be recognized that the sides of the end portions of the tubular passage also may be outwardly flared for the same purpose.

Figure 14:
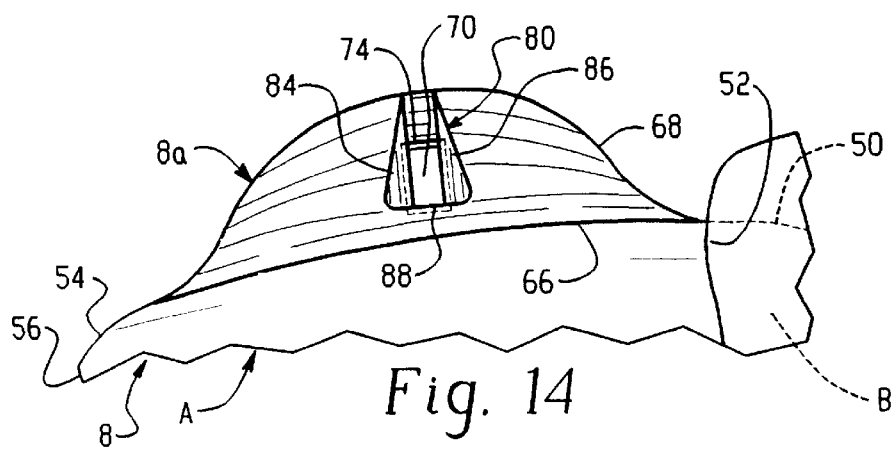
FIG. 14 is a side elevational view taken generally on line 14—14 of FIG. 12.
Figure 16:
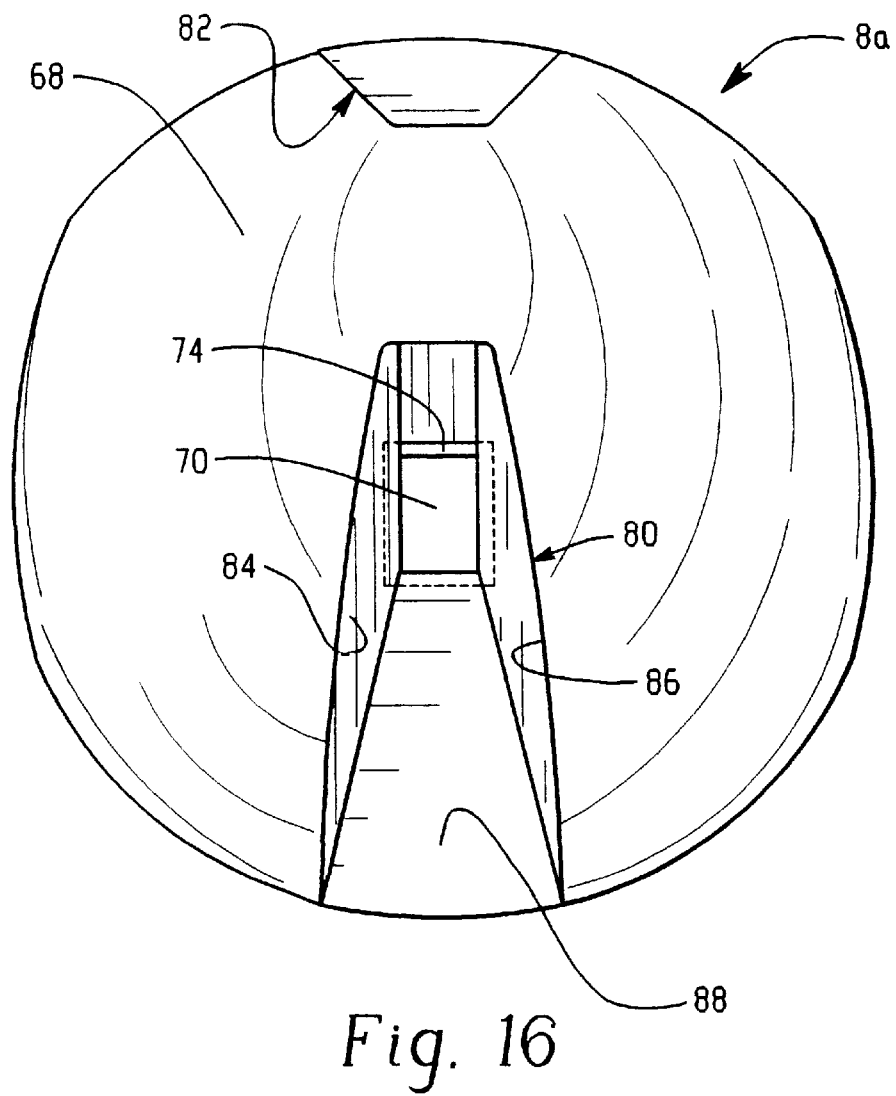
FIG. 16 is a perspective illustration of the improved orthodontic bracket of the present application.

With reference to FIGS. 14–16, opposite grooves 80 and 82 are formed in veneer body facial surface 68 in alignment with the open ends of tube 74. With reference to groove 80, opposite groove sides 84 and 86 diverge from tubular passage 70 to the outer periphery of veneer body 8*a*. Groove bottom 88 also increases in width from tubular passage 70 toward the outer periphery of veneer body 8*a*. Groove sides 84 and 86, along with groove bottom 88, merge into tube 70 as shown in FIGS. 14 and 16. It will be recognized that groove 82 is shaped similarly to groove 80.

A rectangular tubular passage may be molded or broached directly into the veneer body, and a rectangular tube of metal or other suitable material subsequently may or may not be bonded within the passage.

Figure 17:
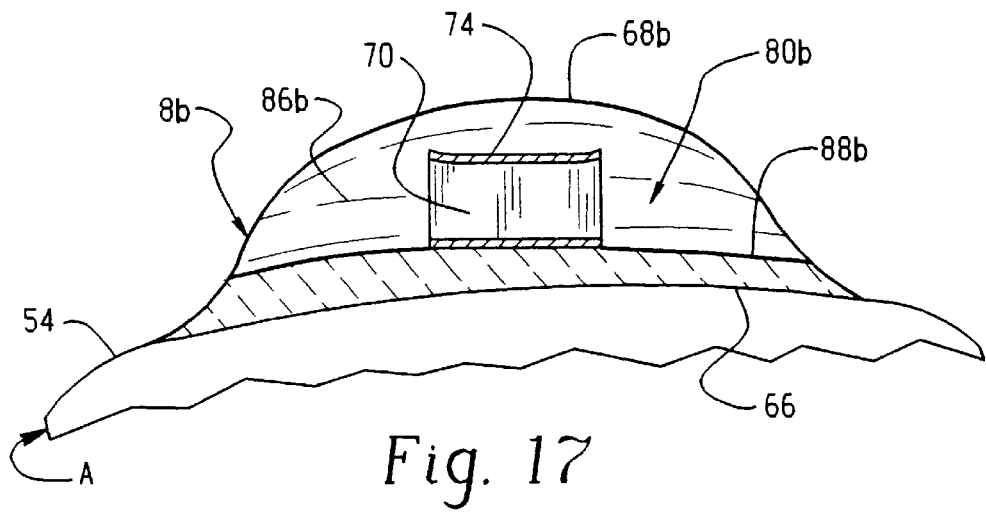
FIG. 17 is a cross-sectional elevational view similar to FIG. 15 and showing another arrangement.
Figure 18:
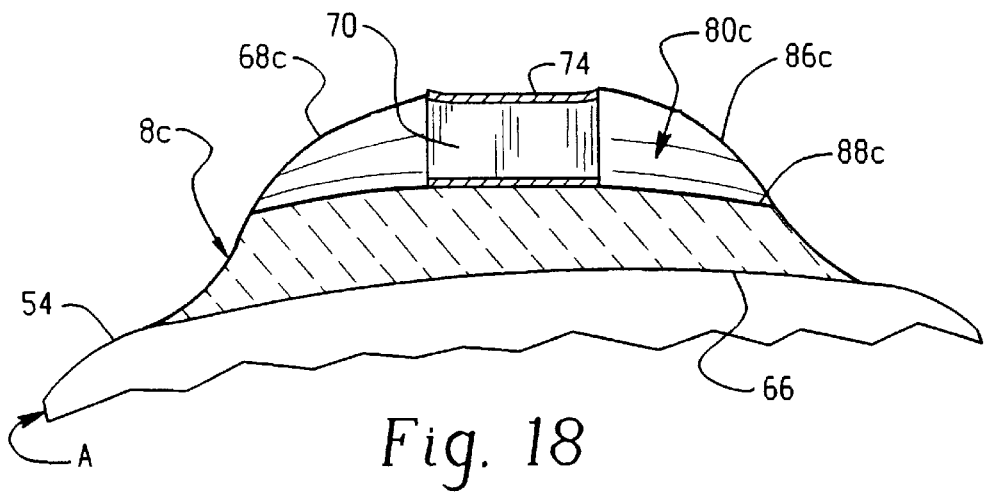
FIG. 18 is a cross-sectional elevational view similar to FIG. 15 and showing still another arrangement.
Figure 19:
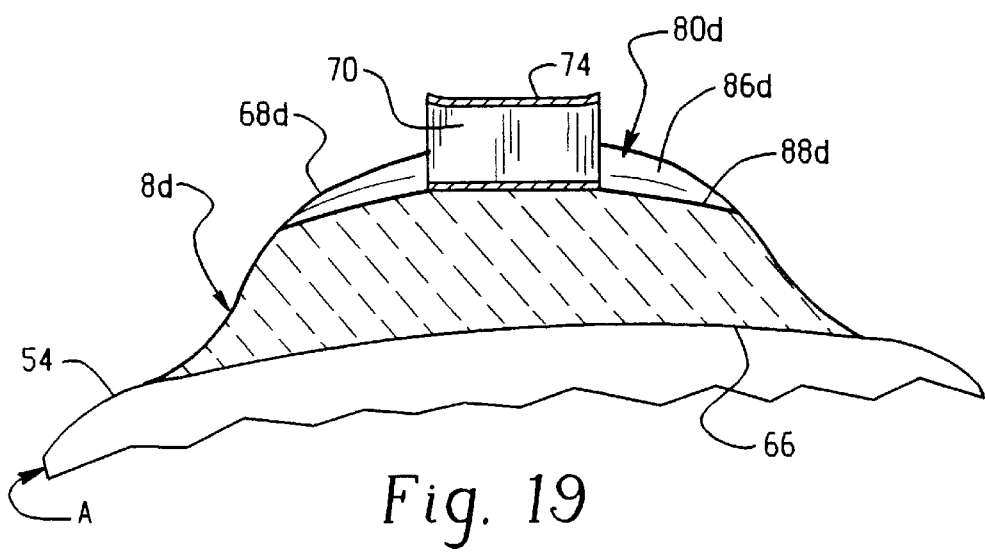
FIG. 19 is a cross-sectional elevational view similar to FIG. 15 and showing a further arrangement.

FIGS. 17–19 show another arrangement in which veneer body 8*b* has a rectangular channel or slot 80*b* machined or milled therein. Slot 80*b* has a slot bottom 88*b* and opposite slot sidewalls, only one of which is shown at 86*b*. Metal tube 74 is a close fit within the slot, and is adhesively bonded to slot bottom 88*b* and to the opposite slot sidewalls. That part of the slot that is located between tube 74 and veneer body outer surface 68*b* subsequently may be filled in with the same material used for the veneer body and machined to the desired contour.

FIG. 18 shows an arrangement in which veneer body 8*c* has a slot 80*c* that is not as deep as slot 80*b* of FIG. 17. The depth of slot 80*c* is such that the outer surface of tube 74 is substantially flush with veneer body outer surface 68*c*. The outer surface of tube 74 may be curved and may also have a color coating thereon to match the appearance of veneer body outer surface 68*c*. Tube 74 is a close fit within slot 80*c*, and is bonded to slot bottom 88*c* and to the opposite slot sidewalls, only one of which is shown at 86*c*.

FIG. 19 shows another arrangement wherein veneer body 8*d* has a shallower rectangular slot 80*d* with a slot bottom 88*d* and opposite slot sidewalls, only one of which is shown at 86*d*. The depth of slot 80*d* is such that at least a portion of tubular passage 70 is located between veneer body outer surface 68*d* and rear bonding surface 66 while the remainder of the passage is located outwardly of veneer body outer surface 68*d*. The extent to which tube 74 projects outwardly from veneer body outer surface 68*d* may be adjusted by varying the depth of slot 80*d*, and little or no projection is the preferred arrangement. However, it is possible to have the entire tubular passage located outwardly of the veneer body outer surface for some situations.

The superflexible archwire used with the orthodontic bracket veneer bodies of the present application is preferably a monofilament of titanium-molybdenum, nickel-titanium or copper-nickel-titanium alloys. Obviously, other alloys and materials also can be used. The archwire is extremely flexible, and can be bent through very sharp angles without suffering permanent deformation beyond its elastic limit. When such an archwire is bent, it wants to assume a smooth uniform curvature or to return to its original smooth U-shaped curvature to relieve the bending and/or torsional stress therein, and this is what applies force to the teeth through the brackets.

The archwire has the same rectangular cross-sectional shape as tube 70 and a slightly smaller size to facilitate threading of the archwire through the tubes. The groove sidewalls and the groove bottom wall that converge toward a rectangular tubular passage 70 facilitate threading the end of a similarly shaped archwire through the tubes.

Figure 20:
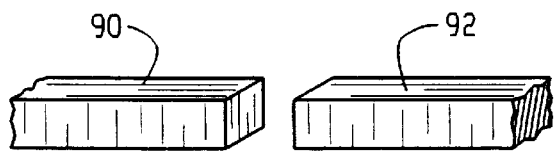
FIG. 20 is a perspective illustration showing end portions of two archwire sections.
Figure 21:
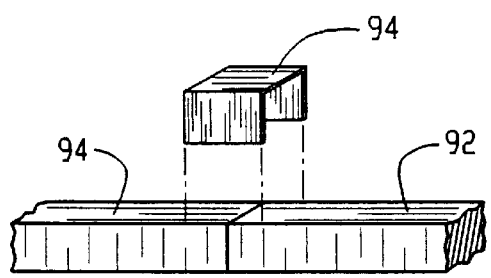
FIG. 21 is a perspective illustration showing the archwire end portions of FIG. 20 butted together for receiving a crimpable connector.
Figure 22:
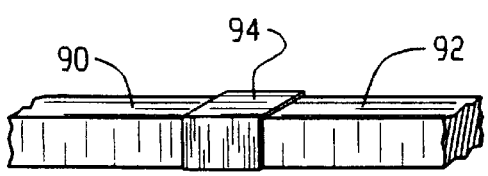
FIG. 22 is a perspective illustration showing end portions of two archwire sections secured together in abutted relationship by a crimped connector.

It may be desirable or necessary in some situations to use heavier archwires that cannot be threaded continuously through all of the tubes in all of the brackets. Two or more archwire lengths are then used and threaded through tubes toward one another from opposite directions. FIGS. 20–22 show adjacent end portions 90 and 92 of heavier adjacent archwires that may have their terminal ends secured together in abutting relationship intermediate adjacent orthodontic brackets by a crimpable connector 94.

FIG. 24 shows a partial model M of a patient's lower dental arch that is made from a dental impression. Dental brackets 19*a*–24*a* are shown attached to the teeth in the model by a releasable adhesive in the proper position for correcting the misaligned teeth. A transparent flexible thermoplastic sheet 102 is then positioned over the dental arch and heated so that it softens and flows over the dental arch and brackets to form a transfer tray 102*a*.

A transparent thermoplastic sheet 103 that is less flexible than sheet 102 is then positioned over transfer tray 102*a* and heated so that it softens and flows over transfer tray 102*a* to form a relatively rigid stabilizing tray 103*a* that is not bonded to transfer tray 102*a* and is readily separable therefrom. Thermoplastic sheet 103 may be of a different and more rigid material than sheet 102, or may be of the same or a similar material and simply be much thicker to provide some rigidity. Stabilizing tray 103*a* is shown in section in FIGS. 25–27 for clarity of illustration.

When the transfer tray 102*a* cools and solidifies, the veneer bodies releasably are trapped in the transfer tray and can be removed from the model teeth along with the transfer tray subsequent to removal of the stabilizing tray as shown in FIG. 26. Dental sealant or other dental adhesive is then applied to the rear attachment surfaces of the veneer bodies and/or the facial surfaces of the teeth, and stabilizing tray 103*a* is repositioned over transfer tray 102*a*. This assembly is then positioned within the patient's mouth and lowered over the patient's dental arch P as shown in FIG. 27 to position the bonding surfaces of the veneer bodies against the facial surfaces of the teeth.

After the dental sealant or adhesive has cured, stabilizing tray 103a and transfer tray 102a can be stripped from both the patient's dental arch P and the orthodontic bracket veneer bodies, leaving the veneer bodies bonded to the facial surfaces of the patient's teeth as shown in FIG. 28.

Figure 23:
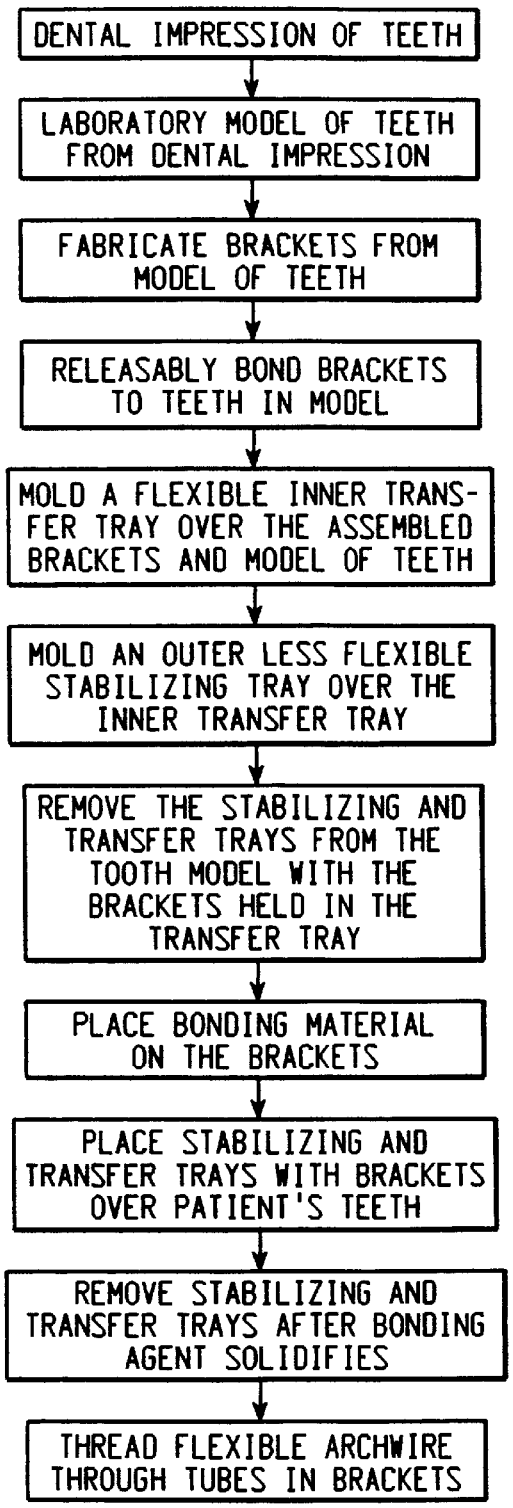
FIG. 23 is a flow diagram showing the steps carried out in practicing the method of the present application.

FIG. 23 shows the steps that are carried out to correct misalignment of teeth in accordance with the present application. Impressions are made of the patient's dental arches and are used to make models of the patient's dental arches. The models are studied to determine the best position and inclination of the tube in each orthodontic bracket veneer body. The facial surfaces of the teeth in the model may be used as mold surfaces or are digitally mapped for molding or machining veneer bodies so that the veneer body bonding surfaces conform to the surface contour of the teeth facial surfaces. The remainder of the veneer body is molded or machined to provide a desired veneer body size and facial surface contour for the particular patient.

In another arrangement, the steps of making an impression of the dental arch and making a model can be eliminated by digitally mapping tooth surfaces to provide a tooth image that is used to fabricate appropriate veneer bodies.

Obviously, instead of using custom fabricated veneer bodies for each patient, sets of universal dental brackets may be provided for use on any patient. The bonding surfaces of the veneer bodies will not conform to the facial surfaces of the patient's teeth as they do in custom fabricated veneer bodies, and the shape of the veneer bodies will not match the patient's teeth as well as in custom fabrication. A mixture of universal and custom fabricated veneer bodies also can be used, with the custom fabricated veneer bodies being made only for the individual teeth requiring special treatment.

With the wisdom teeth removed, each of the upper and lower dental arches have fourteen teeth. One or two additional teeth may be removed in cases of extreme crowding to allow for movement of other teeth. If the incisors or other teeth are badly misaligned, brackets having slots rather than tubular passages may be used on one or more of them. Therefore, the method of the present application uses brackets having tubular passages on the four molars and on at least two additional teeth other than molars in one dental arch for a total of at least six teeth in one dental arch. More preferably, brackets having tubular passages are used on all but 1–3 teeth in a dental arch. Most preferably, brackets having tubular passages are used on all of the teeth in a dental arch.

Brackets having tubular passages normally would be used on the four molars and at least on the bicuspids. Where one or more of the bicuspids have been removed or are so badly misaligned that a slotted bracket must be used, the brackets with tubular passages may be used on only two of the bicuspids. Obviously, one or more of the molars in a person's dental arch besides the wisdom teeth also may be missing so that only two or three brackets with tubular passages would be used on molars while three or four would be used on teeth other than molars for a total of at least six brackets with tubular passages.

The desired orientation of the tubular passage within a veneer body may be determined by using known techniques. By way of example, one arrangement for doing so is explained in U.S. Pat. No. 5,464,349 issued Nov. 7, 1995, the disclosure of which is hereby incorporated herein by reference. The orientation of a tubular passage also may be determined by sectioning a model of a patient's teeth and visually studying the model while manipulating and taking measurements of the model teeth.

The movements that can be imparted to a tooth with forces applied to an orthodontic bracket by an archwire commonly are referred to as torque, tip and angulation. Torque is movement of a tooth about a horizontal axis extending generally parallel to a tooth facial surface in the direction of tooth width. Torque is the movement that would occur by grasping a clinical crown and pushing on the tooth inwardly of a person's mouth or pulling on the tooth outwardly of a person's mouth.

Tip is movement of a tooth about a horizontal axis extending generally perpendicular to a tooth facial surface. Tip is the movement that would occur by grasping a clinical crown and applying force to swing the tooth sideways in either of opposite directions along the width of the tooth.

Angulation is movement of a tooth about a vertical axis extending along the tooth length. Angulation is the movement that would occur by grasping a clinical crown and applying force to rotate the tooth clockwise or counterclockwise about a vertical axis.

Torque, tip and angulation may be considered to involve movements of a tooth about orthogonal X, Y and Z axes, where the X axis is horizontal in the direction of tooth width, the Y axis is vertical in the direction of tooth length, and the Z axis is horizontal in the direction of tooth thickness which is generally perpendicular to a tooth facial surface. Tubular passages in orthodontic brackets are located during fabrication for applying the correct torque, tip and angulation to the tooth on which the bracket will be placed.

Veneer bodies of desired size and shape may be machined from blocks of ceramic, plastic or ceramic/plastic material. Tubular passages may be molded or broached into the blocks prior to machining into veneer bodies of desired size and shape. A tubular passage can be broached into a veneer body after it has been machined to the desired size and shape. A slot may be machined in a veneer body for receiving a separate tube to provide the tubular passage. The orientation of the slot may be varied along with the depth of the slot along its length to achieve the desired orientation of a tube to be adhesively bonded in the slot.

Examples of known arrangements that may be adapted for machining desired veneer bodies are found in U.S. Pat. No. 4,766,704 issued Aug. 30, 1988, U.S. Pat. No. 5,027,281 issued Jun. 25, 1991, and U.S. Pat. No. 5,184,306 issued Feb. 2, 1993. The disclosures of these patents are hereby incorporated herein by reference. Another example of equipment for optically measuring tooth surfaces and grinding dental ceramics is marketed under the trademark CEREC, a trademark of Brains AG, a Swedish corporation.

The veneer bodies of the present application have a maximum thickness that is in alignment with the tubular passage therein. The veneer body thickness gradually decreases in directions outwardly from the area of maximum thickness toward the veneer body outer periphery. The maximum thickness of a veneer body preferably is not greater than about 6 mm, and at least 60% of the total area of a veneer body has a thickness less than 6 mm.

The thickness of a veneer body between the tubular passage and the outer facial surface preferably is greater than the thickness thereof between the passage and the rear bonding surface. Obviously, other arrangements are possible as shown in FIGS. 16 and 17. Each bracket differs from all others in a set in one or more respects. For example, custom fabricated veneer bodies will have different rear bonding surfaces to match the tooth facial surfaces to which they are attached. The size and shape of all brackets also may be different along with the orientation of the tubular passages.

The drawings are not to scale and the veneer body is depicted with an exaggerated thickness relative to its peripheral area for clarity of illustration of the tubular passage and the insert tube that is used to form the tubular passage. An actual veneer body has a much lower profile, and tapers more gradually to an outer feather edge or razor edge at the periphery.

Although the invention has been shown and described with respect to preferred embodiments, it is obvious that equivalent alterations and modifications will occur to others skilled in the art upon the reading and understanding of this specification. The present invention includes all such equivalent alterations and modifications, and is limited only by the scope of the claims.

I claim:

1. An orthodontic bracket comprising a non-metallic veneer body having a rear bonding surface that is bondable to a tooth facial surface and an opposite body facial surface that supplants a tooth facial surface, said veneer body having an outer periphery that includes opposite gum and terminal end portions and opposite side portions, said veneer body having a single archwire receiving tubular passage located intermediate said gum and terminal end portions of said outer periphery, said tubular passage having opposite open ends that open outwardly toward and are spaced inwardly from said opposite side portions of said outer periphery, at least a portion of said tubular passage being located within said veneer body between said rear bonding surface and said body facial surface, and said body facial surface being uninterrupted by any continuous archwire receiving slot that is outwardly open along its entire length at said body facial surface to receive a portion of an archwire by movement of the archwire in a direction toward said body facial surface and into the slot.

2. The bracket of claim 1 wherein said tubular passage is formed integrally in said veneer body.

3. The bracket of claim 1 wherein said tubular passage is defined by the interior surface of a tube secured to said veneer body.

4. The bracket of claim 1 wherein said tubular passage has a rectangular cross-sectional shape.

5. The bracket of claim 4 wherein said rectangular cross-sectional shape is square.

6. The bracket of claim 4 wherein said rectangular cross-sectional shape includes short and long sides and said tubular passage is positioned with said long sides extending in a direction between said body facial surface and said rear bonding surface.

7. The bracket of claim 1 wherein said rear bonding surface has an area within said outer periphery that is at least 50% of the area of a tooth facial surface to which said veneer body is adapted to be attached.

8. The bracket of claim 1 wherein said veneer body has a non-uniform thickness that includes an area of maximum thickness located inwardly of said outer periphery in alignment with said tubular passage, and said veneer body gradually decreasing in thickness from said area of maximum thickness toward said outer periphery.

9. The bracket of claim 1 wherein said tubular passage has a longitudinal axis and the distance from said rear attachment surface to said longitudinal axis is not greater than 3 mm.

10. The bracket of claim 9 wherein said distance is not greater than 2 mm.

11. The bracket of claim 1 wherein said veneer body has a maximum thickness that is not greater than 6 mm.

12. The bracket of claim 11 wherein at least 60% of the area of said veneer body has a thickness less than 4 mm.

13. The bracket of claim 1 wherein said tubular passage is located entirely within said veneer body between said rear bonding surface and said body facial surface.

14. The bracket of claim 13 wherein said veneer body has an area of maximum thickness between said tubular passage and said veneer body facial surface that is greater than the thickness of said veneer body between said tubular passage and said rear bonding surface.

15. The bracket of claim 1 wherein said tubular passage has a length between said open ends that is not less than 2 mm and is not greater than 60% of the width of said veneer body across said opposite side portions thereof.

16. A set of at least eight orthodontic brackets adapted to be applied to at least eight teeth in an upper or lower human jaw, each tooth having a root, a terminal end, opposite sides and a facial surface, each of said brackets being prefabricated with the hereinafter defined physical characteristics prior to application thereof to a tooth, each of said brackets having a rear bonding surface that is adapted to be bonded to a tooth facial surface, each bracket having a single archwire receiving peripherally continuous preformed tubular passage extending in a direction between said tooth opposite sides, each of said brackets having an outer periphery and an outer surface that is continuous within said outer periphery and being of the same material throughout its extent within said outer periphery, and said tubular passage in each of said brackets being the sole means on each bracket for retaining an archwire thereto and for transferring forces from the archwire to a tooth through the bracket.

17. The bracket set of claim 16 wherein each said bonding surface on each said bracket covers at least 50% of the tooth facial surface to which it is adapted to be bonded.

18. The bracket set of claim 16 wherein each said bracket comprises a non-metallic thin veneer body.

19. The bracket set of claim 16 wherein each said bracket comprises a thin veneer body having a maximum thickness not greater than 6 mm.

20. The bracket set of claim 19 wherein at least 60% of the area of each said bracket has a thickness less than 4 mm.

21. The bracket set of claim 16 wherein the distance from said rear bonding surface to the centerline of a tubular passage is not greater than 3 mm.

22. The bracket set of claim 16 including an archwire extending through each said tubular passage in each said bracket.

23. The bracket set of claim 16 wherein each said bracket is different from all other brackets in said bracket set.

24. The bracket set of claim 16 wherein each said rear bonding surface on each said bracket is shaped to closely fit a different tooth facial surface.

25. The bracket set of claim 16 wherein each said bracket facial surface has a different surface shape to substantially supplant a different tooth facial surface.

26. The bracket set of claim 16 wherein said rear bonding surface has a width that is at least 50% of the distance across the opposite sides of a tooth to which said rear bonding surface is adapted to be bonded.

27. For use in an upper or lower human jaw having at least thirteen teeth, each tooth having a tooth facial surface, an orthodontic bracket adapted to be bonded to at least six of said tooth facial surfaces including at least two tooth facial surfaces on teeth other than molars, each said bracket having a single archwire receiving peripherally continuous preformed tubular passage therein with opposite open ends, and said tubular passage in each of said brackets being the sole means on each bracket for retaining an archwire thereto and for transferring forces from the archwire to a tooth through the bracket.

28. The jaw of claim 27 wherein each said bracket comprises a non-metallic thin veneer body.

29. The jaw of claim 28 wherein each said bracket has a rear bonding surface area that covers at least 50% of a tooth facial surface area to which it is adapted to be attached.

30. The jaw of claim 27 wherein said brackets are adapted to be bonded to at least molars and bicuspids.

31. The jaw of claim 30 wherein said brackets are adapted to be bonded to teeth in addition to molars and bicuspids.

32. The jaw of claim 27 therein at least ten of said thirteen teeth are adapted to have said brackets bonded thereto, and an archwire threaded through said tubular passages in all of said brackets.

33. A method of correcting misalignment of teeth in an upper or lower human jaw comprising the steps of providing at least six orthodontic brackets having peripherally continuous tubular passages therein, attaching said brackets to facial surfaces of at least six teeth that include teeth other than molars in an upper or lower human jaw with the tubular passages extending transversely of the tooth length, and threading a flexible archwire through all of the tubular passages.

34. The method of claim 33 wherein said step of attaching brackets is carried out by attaching brackets to facial surfaces of at least molars and bicuspids.

35. The method of claim 33 wherein said step of attaching brackets is carried out by attaching brackets to facial surfaces of at least ten teeth.

36. A method of correcting misalignment of teeth in an upper or lower human jaw comprising the steps of making a dental impression of the teeth, making a model of the teeth from the dental impression, fabricating at least six orthodontic brackets for bonding to at least six of the teeth that include teeth other than molars, fabricating each bracket with a bonding surface shaped to substantially match the facial surface shape of a tooth to which it is to be attached, fabricating each bracket with a tubular passage, bonding the brackets to facial surfaces of the teeth from which the dental impression was formed, and threading a flexible archwire through all of the tubular passages in all of the brackets.

37. A method of correcting misalignment of incisors and cuspids in a human jaw comprising the steps of attaching orthodontic brackets having tubular passages therein to facial surfaces of at least some of the incisors and cuspids with the tubular passages extending transversely of the length of the incisors and cuspids, and threading a flexible archwire through all of the tubular passages subsequent to the step of attaching the orthodontic brackets.

38. An orthodontic bracket comprising a non-metallic veneer body having a rear bonding surface that is bondable to a tooth facial surface and an opposite body facial surface that supplants a tooth facial surface, said veneer body having an outer periphery that includes opposite gum and terminal end portions and opposite side portions, said veneer body having a tubular passage located intermediate said gum and terminal end portions of said outer periphery, said tubular passage having opposite open ends that open outwardly toward and are spaced inwardly from said opposite side portions of said outer periphery, at least a portion of said tubular passage being located within said veneer body between said rear bonding surface and said body facial surface, and said body facial surface having grooves therein aligned with said open ends of said tubular passage.

39. An orthodontic bracket comprising a non-metallic veneer body having a rear bonding surface that is bondable to a tooth facial surface and an opposite body facial surface that supplants a tooth facial surface, said veneer body having an outer periphery that includes opposite gum and terminal end portions and opposite side portions, said veneer body having a tubular passage located intermediate said gum and terminal end portions of said outer periphery, said tubular passage having opposite open ends that open outwardly toward and are spaced inwardly from said opposite side portions of said outer periphery, at least a portion of said tubular passage being located within said veneer body between said rear bonding surface and said body facial surface, said tubular passage having a longitudinal axis and said body facial surface having grooves therein aligned with said opposite open ends of said tubular passage, and said grooves having groove surfaces that diverge from said longitudinal axis in a direction from said open ends toward said opposite side portions of said veneer body.

40. An orthodontic bracket comprising a non-metallic veneer body having a rear bonding surface that is bondable to a tooth facial surface and an opposite body facial surface that supplants a tooth facial surface, said veneer body having an outer periphery that includes opposite gum and terminal end portions and opposite side portions, said veneer body having a preformed tubular archwire receiving passage located intermediate said gum and terminal end portions of said outer periphery, said tubular archwire receiving passage having a rectangular cross-sectional shape and opposite open ends that open outwardly toward and are spaced inwardly from said opposite side portions of said outer periphery, at least a portion of said tubular passage being located within said veneer body between said rear bonding surface and said body facial surface.

41. The bracket of claim 40 wherein said tubular passage is integral with said veneer body and is located entirely between said rear bonding surface and said body facial surface.

42. The bracket of claim 40 wherein said tubular passage is defined by the interior of a separate tubular member that is secured to said veneer body.

\* \* \* \* \*